United States Patent
Chen et al.

(10) Patent No.: US 8,142,999 B2
(45) Date of Patent: Mar. 27, 2012

(54) HLA ALLELES ASSOCIATED WITH ADVERSE DRUG REACTIONS AND METHODS FOR DETECTING SUCH

(75) Inventors: Yuan-Tsong Chen, Taipei (TW); Shuen-Iu Hung, Chang-Hwa (TW); Chih-Lung Shen, Taipei (TW); Chi-Feng Chang, Taipei (TW); Hsin-Yu Lin, Taipei (TW); Wei-Hsuan Chen, Lioujia Township, Tainan County (TW)

(73) Assignees: Academia Sinica, Taipei (TW); Pharmigene, Inc., Taipei (TW)

( * ) Notice: Subject to any disclaimer, the term of this patent is extended or adjusted under 35 U.S.C. 154(b) by 0 days.

(21) Appl. No.: 13/100,665

(22) Filed: May 4, 2011

(65) Prior Publication Data

US 2011/0212439 A1 Sep. 1, 2011

Related U.S. Application Data

(63) Continuation of application No. 11/747,674, filed on May 11, 2007, now Pat. No. 7,943,309.

(60) Provisional application No. 60/800,121, filed on May 11, 2006.

(51) Int. Cl.
  *C12Q 1/68* (2006.01)
  *C12P 19/34* (2006.01)
  *C12M 1/34* (2006.01)
(52) U.S. Cl. .................. 435/6; 435/91.2; 435/287.1
(58) Field of Classification Search .................. None
  See application file for complete search history.

(56) References Cited

U.S. PATENT DOCUMENTS

| 5,550,039 A | 8/1996 | Trachtenberg |
| 5,883,238 A | 3/1999 | Andrien |
| 6,583,139 B1 | 6/2003 | Thorsett et al. |
| 7,470,513 B2 | 12/2008 | Chen et al. |
| 2005/0100926 A1 | 5/2005 | Chen et al. |

OTHER PUBLICATIONS

Wang et al. Seizure 2010 vol. 19 p. 562-566.*
Alfirevic A, et al "HLA-B locus in Caucasian patients with caramazepine hypersensitivity." *Pharmacogenomics*. Sep. 2006; 7(6):813-8.
Bigby et al. (1986) Drug-induced cutaneous reactions. A report from the Boston Collaborative Drug Surveillance Program on 15,438 consecutive inpatients, 1975 to 1982. *JAMA*. 256(24):3358-3363.
Carbamazepine, available online at http://www.mentalhealth.com/drug/p30-t01.html> pp. 1-17, Jan. 18, 2008.
Chan et al. "HLA and allopurinol drug eruption" *Dermatologica*. 1989, 179(1):32-3.
Chung et al (2004). Medical genetics: a marker for Stevens-Johnson syndrome. *Nature*. 428(6982):486.
Deng et al. LOD score exclusion analyses for candidate genes using random population samples. *Ann Hum Genet*. May 2001;65(Pt 3):313-29.
Edwards et al. Concordance of primary generalized epilepsy and carbamazepine hypersensitivity in monozygotic twins. *Postgrad Med J*. 1999, 75(889):680-1.
Feltkamp et al. Spondyloarthropathies in eastern Asia. *Curr Opin Rheumatol*. 2001, 13(4):285-90.
Gennis et al. Familial occurrence of hypersensitivity to phenytoin. *Am J Med*. 1991, 91(6):631-4.
Green et al. Genetic analysis of microsomal epoxide hydrolase in patients with carbamazepine hypersensitivity. *Biochem Pharmacol*. 1995, 50(9):1353-9.
Gumperz et al. (1995). The Bw4 public epitope of HLA-B molecules confers reactivity with natural killer cell clones that express NKB1, a putative HLA receptor. *J Exp Med*. 181(3):1133-1144.
Gut, J. (2002). Severe adverse drug reactions and theragenomics. *Business Briefing Pharmatech*. Retrieved from the Internet: URL: http://jlglex.com/TheragenomicArticle3.pdf> Retrieved on Dec. 19, 2007.
Hari et al. T cell involvement in cutaneous drug eruptions. *Clin Exp Allergy*. 2001, 31(9):1398-1408.
Hildesheim et al. (2002). Association of HLA class I and II alleles and extended haplotypes with nasopharyngeal carcinoma in Taiwan. *J Natl Cancer Inst*. 94(23):1780-1789.
Hiratsuka M., et al, Competitive allele-specific short oligonucleotide hybridization (CASSOH) with enzyme-linked immunosorbent assay (ELISA) for the detection of pharmacogenetic single nucleotide polymorphisms (SNPs). J of Biochemical and Biophysical Methods, 67:87-94 (2006).
Hung et al. HLA-B genotyping to detect carbamazepine-induced Stevens-Johnson syndrome: implications for personalizing medicine. *Personalized Medicine*. Aug. 2005, vol. 2, No. 3, pp. 225-237.
Juppner, H. Functional properties of the PTH/PTHrP receptor. *Bone*. Aug. 1995; 17(2 Suppl):39S-42S.
Khan, MA. Update: the twenty subtypes of HLA-B27. *Curr Opin Rheumatol*. 2000, 12(4):235-8.
Lazarou et al. (1998) Incidence of adverse drug reactions in hospitalized patients: a meta-analysis of prospective studies. *JAMA*. 279(15):1200-1205.
Leeder, JS. Mechanisms of idiosyncratic hypersensitivity reactions to antiepileptic drugs. *Epilepsia*. 1998, 29 Suppl 7:S8-16.
Lonjou et al. A marker for Stevens-Johnson syndrome . . . : ethical matters. *Pharmacogenomics Journal*. (2006) 6, 265-268; published online Jan. 17, 2006.
Mallal et al. (2002). Association between the presence of HLA-B*5701, HLA-DR7, and HLA-DQ3 and hypersensitivity to HIV-I reverse transcriptase inhibitor abacavir. *Lancet*. 359(9308):727-732.
Naisbitt et al. Hypersensitivity reactions to carbamazepine: characterization of the specificity, phenotype, and cytokine profile of drug-specific T cell clones. *Mol Pharmacol*. 2003, 63(3):732-41.

(Continued)

*Primary Examiner* — Katherine Salmon
(74) *Attorney, Agent, or Firm* — Occhiuti Rohlicek & Tsao LLP

(57) ABSTRACT

This invention relates to a method of determining the presence of certain HLA alleles, such as HLA-B*1502 or HLA-B*5801, and a kit for carrying out this method. Also disclosed is a method for assessing whether a patient is at risk for developing adverse drug reactions (e.g., Stevens-Johnson syndrome, toxic epidermal necrolysis, or hypersensitivity syndrome) based on the presence or absence of a genetic marker (e.g., HLA-B*1502, HLA-B*5801, or HLA-B*4601).

8 Claims, 3 Drawing Sheets

OTHER PUBLICATIONS

Nassif et al. (2002). Drug specific cytotoxic T-cells in the skin lesions of a patient with toxic epidermal necrolysis. *J Invest Dermatol.* 118(4):728-733.

Pichler et al. High IL-5 production by human drug-specific T cell clones. *Int Arch Allergy Immunol.* 1997, 113(1-3):177-80.

Pirmohamed et al. TNFα promoter region gene polymorphisms in carbamazepine-hypersensitive patients. *Neurology.* 2001, 56(7):890-6.

Pirmohamed et al (2003). Adverse drug reactions: back to the future. *Br J Clin Pharmacol.* 55(5):486-492.

Romphruk et al (2003). HLA-B*15 subtypes in the population of north-eastern Thailand. *Eur J Immunogenet.* 30(2):153-158.

Roujeau et al. HLA phenotypes and bullous cutaneous reactions to drugs. *Tissue Antigens.* 1986, 28(4):251-4.

Roujeau et al. Genetic susceptibility to toxic epidermal necrolysis. *Arch Dermatol.* 1987, 123(9):1171-3.

Roujeau, JC. The spectrum of Stevens-Johnson syndrome and toxic epidermal necrolysis: a clinical classification. *J Invest Dermatol.* 1994, 102(6):28S-30S.

Roujeau et al. Severe adverse cutaneous reactions to drugs. *N Engl J Med.* 1994, 331(19):1272-85.

Roujeau et al. Medication use and the risk of Stevens-Johnson syndrome or toxic epidermal necrolysis. *N Engl J Med.* 1995, 333(24):1600-7.

Sankar, P., Medline definitions of race and ethnicity and their application to genetic research. *Nature Genetics* (2003), vol. 34, p. 119.

Shirato et al. Stevens-Johnson syndrome induced by methazolamide treatment. *Arch Ophthalmol.* 1997, 115(4):550-3.

Svensson et al. Cutaneous drug reactions. *Pharmacol Rev.* 2000, 53(3):357-379.

Thisted, RA. What is a P-value? (1998). Available online at http://www.stat.uchicago.edu/~thisted/Distribute/pvalue.pdf> Retrieved on Dec. 19, 2007.

Wolkenstein et al. A slow acetylator genotype is a risk factor for sulphonamide-induced toxic epidermal necrolysis and Stevens-Johnson syndrome. *Pharmacogenetics.* 1995, 5(4):255-8.

Yates et al. Molecular diagnosis of thiopurine S-methyltransferase deficiency: genetic basis for azathioprine and mercaptopurine intolerance. *Annals of Internal Med.* 1997, 126(8):608-14.

Hung et al., Pharmacogenetics and Genomics, vol. 16(4), pp. 297-306 (2006).

Hung et al., Proceedings of the National Academy of Sciences of the United States of America, vol. 102(11), pp. 4139-7139 (2005).

Misra, et al. (Postgrad Med J 2003 vol. 39 p. 703).

Chung, et al. (Nature Apr. 2004 vol. 428 p. 486).

Futami, et al. (Digestive Diseases and Sciences 1995 vol. 40 p. 814).

Leeder (Epilepsia 1998 vol. 39 Suppl 7:S8-16).

Lim, et al. (Neurology Asia 2008 vol. 13 p. 15).

* cited by examiner

HLA-B*1502: exon2+3 546 bp  ▓ junction  intron 245 bp

GCT CCC ACT CCA TGA GGT ATT TCT ACA CCC CCA TGT CCC CGG CCC GCT GGG AGC CCC GCT TCA TCG CCC GGG CCC CAT

GCT AGG GCC ACA CCC AGT TCG TGA GGT TCG ACA GCG ACG CCG CGG GTC CGA TGG CGG ACA CAC AGA CTT ACC GAG

GGA TAG AGC AGG AGG GCC CGG AGT ATT GGG ACC GG(A AC)A CAC AGA TCT(CCA ACA)A CAC AGA CTT ACC GAG
                                              1                2

AGA GCC TGG GGA ACC TGC GCT ACT ACA ACC AGA GCC AGG CGG CTC ACA(TcA)TCC AGA GGA TGT A(T)G
                                                                 3                    4

Contain 245 bp in the blank region (not listed in detail)

GCT CCC ACG TGG GGC CGG ACG GGC TCC TCC CGG AC(T)ATC ACC AGT CCC CCT ACC ACC GCA AGG ATT ACA TCG CCC
                                              5

TGA AGG AGG ACC TGC GCT CCT GGA CCA CGG CAG ACA CGG CTC AGA TCA CCC AGG CGA AGT GGG AGG CCG CGG CGG

GTC AGG CGG AGC AG(CT)GA GAG CCT ACC TGG AGG ACC TGC AGG ACC TGG AGT GGC TCC GCA GAT ACC TGG AGA ACG GGA AGG
                   6

AGA CCC TGC AGC GCG

Figure 1

HLA-B*5801 exon2+3 546 bp   junction   intron-245 bp

GCT CCC ACT CCA TGA GGT ATT TCT ACA CCG CCA TGT CCC GGG GCC CGG GGC GGG AGC CCC GCT TCA
TCG CAG TGG GCT ACG TGG ACG ACA CCC AGT TCG TGA GGT TCG ACA GCG ACG CCG CGA GTC CGA GG
(AC)GGA GC CCC GGG CGC CAT GGA TAG AGC AGG AGG GGC CGG AGT ATT GGG ACG GGG AGA CAC
GGA A(CATG)A AGG CCT CCG G C AGA CTT ACC GAG AGA ACC TGC GGA (ATCG CGC TCC) CT ACT ACA
ACC AGA GCG AGG CGG GT CTC A (CATCA TCC) AGA GGA TGT ATG GCT GCG AC (C) TGG GGC C
———Contain 245 bp in the blank region (not listed in detail)———
GACG GGC GCC TCC TCC GCG GGC GGC (ATG ACCAGTC) CG CCT ACG ACG GCA AGG ATT ACA TCG CCC TGA
ACG AGG ACC TGA GCT CCT GGA CCG CGG ACA CCGCGG CTC AGA TCA CCC AGC GCA AGT GGG
AGG CGG CCC GTG TGG CGG AGC AGC TGA GAG CCT ACC TGG AGG GCC TGT GCG TGG AGT GGC TCC
GCA GAT ACC TGG AGA ACG GGA AGG AGA CGC TGC AGC GCG CGG.

Figure 2

SEQUENCE LISTING

```
<160> NUMBER OF SEQ ID NOS: 4

<210> SEQ ID NO 1
<211> LENGTH: 297
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 1
gctcccactc catgaggtat ttctacaccg ccatgtcccg gcccggccgc ggggagcccc      60
gcttcatcgc agtgggctac gtggacgaca cccagttcgt gaggttcgac agcgacgccg     120
cgagtccgag gatggcgccc cgggcgccat ggatagagca ggaggggccg gagtattggg     180
accggaacac acagatctcc aagaccaaca cacagactta ccgagagagc ctgcggaacc     240
tgcgcggcta ctacaaccag agcgaggccg ggtctcacat catccagagg atgtatg       297

<210> SEQ ID NO 2
<211> LENGTH: 249
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 2
gctgcgacgt ggggccggac gggcgcctcc tccgcggcta tgaccagtcc gcctacgacg      60
gcaaggatta catcgccctg aacgaggacc tgagctcctg gaccgcggcg gacacggcgg     120
ctcagatcac ccagcgcaag tgggaggcgg cccgtgaggc ggagcagctg agagcctacc     180
tggagggcct gtgcgtggag tggctccgca gatacctgga gaacgggaag gagacgctgc     240
agcgcgcgg                                                             249

<210> SEQ ID NO 3
<211> LENGTH: 313
<212> TYPE: DNA
<213> ORGANISM: Artificial Sequence
<220> FEATURE:
<223> OTHER INFORMATION: Description of Artificial Sequence: Synthetic
      construct
```

-continued

```
<400> SEQUENCE: 3
gctcccactc catgaggtat ttctacaccg ccatgtcccg gcccggccgc ggggagcccc      60
gcttcatcgc agtgggctac gtggacgaca cccagttcgt gaggttcgac agcgacgccg     120
cgagtccgag gacggagccc cgggcgccat ggatagagca ggaggggccg gagtattggg     180
acggggagac acggaacatg aaggcctccg cgcagactta ccgagagaac ctgcggatcg     240
cgctccctac tacaaccaga gcgaggccgg gtctcacatc atccagagga tgtatggctg     300
cgacctgggg ccc                                                        313

<210> SEQ ID NO 4
<211> LENGTH: 232
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 4
gacgggcgcc tcctccgcgg gcatgaccag tccgcctacg acggcaagga ttacatcgcc      60
ctgaacgagg acctgagctc ctggaccgcg gcggacaccg cggctcagat cacccagcgc     120
aagtgggagg cggcccgtgt ggcggagcag ctgagagcct acctggaggg cctgtgcgtg     180
gagtggctcc gcagatacct ggagaacggg aaggagacgc tgcagcgcgc gg             232
```

HLA ALLELES ASSOCIATED WITH ADVERSE DRUG REACTIONS AND METHODS FOR DETECTING SUCH

CROSS-REFERENCE TO RELATED APPLICATIONS

This application is a continuation of U.S. patent application Ser. No. 11/747,674, filed May 11, 2007, now issued as U.S. Pat. No. 7,943,309, which claims the benefit of U.S. patent application Ser. No. 60/800,121, filed May 11, 2006. The contents of both prior applications are incorporated herein by reference in their entirety.

BACKGROUND

An adverse drug reaction (ADR) is an undesired and unintended effect of a drug. In particular, an adverse drug reaction occurs at doses used for prophylaxis, diagnosis or therapy. According to a widely cited meta-analysis, ADRs were ranked between the fourth and sixth most common cause of death (Lazarou et al., JAMA, 279(15):1200-1205, 1998). Cutaneous ADRs account for about 2-3% of all hospital admissions (Bigby et al., JAMA, 256(24):3358-3363, 1986). They range from mild maculopapular (MPE), with increasing severity, to life-threatening ADRs, such as hypersensitivity syndrome (HSS), Stevens-Johnson syndrome (SJS) and toxic epidermal necrolysis (TEN; Lyell's syndrome). The mortality rate of the latter can be as high as 40%.

HSS is characterized by multi-organ involvements (e.g. hepatitis or nephritis) accompanied with systemic manifestations (e.g. fever, arthragis, eosinophilia and lymphadenopathy) in additional to skin rashes (Roujeau et al., N. Engl. J. Med., 331:1272-1285, 1994). SJS and TEN are immune-complex-mediated hypersensitivity disorders characterized by rapid development of blistering exanthema of purpuric macules and target-like lesions accompanied with mucules involvement and skin detachments (Roujeau et al. J Invest Dermatol, 1994, 102:28S-30S). They are caused mostly by drugs, such as sulfonamides, anticonvulsants, allopurinol, nonsteroidal anti-inflammatory drugs, and antimalarials (Roujeau et al., N. Engl. J. Med., 333(24):1600-1607, 1995). In Taiwan, anticonvulsants (e.g., CBZ, phenytoin and phenobarbital) and allopurinol are the most common drugs causing SJS/TEN.

Recent developments of pharmacogenomics have implied that the susceptibility to ADRs is associated with particular genetic alleles. For example, genomic polymorphisms of the thiopurine methyltransferase gene were found to be closely related to ADRs induced by azathioprine, a drug for rheumatologic diseases or cancer (Yates et al., Ann. Intern. Med., 126(8):608-614, 1997). It is also suggested that the susceptibility to SJS/TEN/HSS induced by certain drugs is genetically determined (Gennis M A, Am. J. Med., 91(6):631-634, 1991; Edwards S G, Postgrad. Med. J., 75(889):680-681, 1999). However, the exact responsible genetic factors have yet to be identified.

These pharmacogenomics studies suggest that detecting ADR-associated alleles in a patient is a useful approach for assessing whether that patient is at risk for developing ADRs. This kind of molecular diagnostics certified by Clinical Laboratory Improvement Amendments is now offered by reference laboratories in the US and Europe.

To determine the presence of a particular genetic allele, one or more allelic-specific nucleotide need to be detected. In many cases, multiple regions within the allele must be targeted to achieve an accurate determination. For example, currently available methods for determining an HLA-B allele (e.g., HLA-B*1502 or HLA-B*5801) requires detecting at least 6 regions within that allele.

SUMMARY OF THE INVENTION

The present invention provides a method of predicting the risk of a patient for developing adverse drug reactions, particularly SJS, TEN, or HSS. It was discovered that HLA-B*1502 is associated with SJS/TEN induced by a variety of drugs, e.g., carbamazepine (CBZ). In addition, HLA-B*5801 is particularly associated with SJS/TEN induced by allopurinol. HLA-B*5801 is also associated with allopurinol-induced HSS. Milder cutaneous reactions induced by CBZ, such as maculopapular rash, erythema multiforme, urticaria, and fixed drug eruption, are particularly associated with HLA-B*4601.

Accordingly, the present application provides a method of assessing the risk of a patient for developing an adverse drug reaction in response to a drug, including performing HLA typing using a biological sample from the patient. Any HLA allele that is associated with the ADR with a sensitivity of at least about 40% can be used as the risk factor in the present invention. Preferably, the sensitivity of the risk factor is at least about 50%, 60%, 70%, 80%, 85% or 90%. More preferably, the sensitivity is at least 95%. The drug is preferably selected from the group consisting of CBZ, oxcarbazepine (brand name: trileptal), licarbazepine, allopurinol, phenytoin, sulfasalazine, amoxicillin, ibuporfen and ketoprofen. Alternatively, the drug is preferably not a nonsteroidal anti-inflammatory drug. Preferably, an HLA-B allele is the risk factor.

Assessing the risk of a patient for developing an adverse drug reaction in response to a drug, can be accomplished by determining the presence of an HLA-B allele selected from the group consisting of HLA-B*1502, HLA-B*5801 and HLA-B*4601, wherein the presence of the HLA-B allele is indicative of a risk for an adverse drug reaction. The drug can be selected from the group consisting of CBZ, oxcarbazepine, licarbazepine, allopurinol, oxypurinol, phenytoin, sulfasalazine, amoxicillin, ibuprofen, and ketoprofen.

The adverse drug reaction can be a cutaneous adverse drug reaction, such as SJS, TEN, or HSS. In one embodiment, the drug is selected from CBZ, oxcarbazepine, licarbazepine, and the allele is HLA-B*1502. In another embodiment, HLA-B*5801 is used to predict the risk for SJS, TEN, or HSS, and the drugs can be selected from allopurinol or oxypurinol. Other subtypes of HLA-B15, B58 or B46, such as HLA-B*1503 or *1558, can also be used to predict the risk for developing an ADR.

A genetic allele can be detected by direct detection of regions/nucleotides within the allele using genomic DNAs prepared from biosamples, e.g., blood, saliva, urine or hair. The allele can also be detected by, for example, serological or microcytotoxicity methods. It also can be determined by detecting an equivalent genetic marker of the allele, which can be, e.g., an SNP (single nucleotide polymorphism), a microsatellite marker or other kinds of genetic polymorphisms. In other words, the presence of the HLA-B*1502, 5801 or 4601 haplotype, rather than the allele per se, is indicative of a risk for adverse drug reactions. Exemplary equivalent genetic markers of HLA-B B*1502 haplotype include DRB1*1202, Cw*0801, Cw*0806, A*1101, and MICA*019. Exemplary equivalent genetic markers of HLA-B*5801 includes HLA-A*3303, Cw*0302, DRB1*0301, and MICA*00201.

Another aspect of the present invention is a method of pharmacogenomics profiling. This method includes determining the presence of at least one HLA-B allele selected from the group consisting of HLA-B*1502, HLA-B*5801, and HLA-B*4601. In one example, the presence of at least two alleles selected from the group is determined, such as HLA-B*1502 and HLA-B*5801. In another example, the presence of all three alleles is determined. The method can optionally comprise the determination of other genetic factors. Those other genetic factors can be associated with the predisposition for any disease or medical condition, including ADRs. For example, these other genetic factors can be selected from the group consisting of thiopurine methyltransferase and the genes for the long-QT syndrome.

Also within the scope of this invention is a method for determining whether a patient carries HLA-B*1502 or HLA-B*5801. This method includes the steps of: (1) detecting a first region selected from either Regions 1-6 of HLA-B*1502 or Regions 1-6 of HLA-B*5801, (2) detecting a second region selected from either Regions 1-6 of HLA-B*1502 or Regions 1-6 of HLA-B*5801, the second region being different from the first region, and (3) determining whether the patient carries the allele of interest, the presence of the first and second regions indicating that the patient carries HLA-B*1502 or HLA-B*5801. These regions can be detected by Real-Time PCR or Competitive Sequence-Specific Oligonucleotide hybridization assay coupled with ELISA (CSSO-ELISA). In one example, detecting two regions selected from Regions 1-6 of HLA-B*1502 or from Regions 1-6 of HLA-B*5801 is sufficient to determine the presence or absence of HLA-B*1502 or HLA-B*5801. Alternatively, three or more regions within HLA-B*1502 or HLA-B*5801 are detected.

Detection of Region 1, Region 2, and Region 3 of HLA-B*1502 can be achieved respectively by identifying nucleotides at positions 1 and 3 within Region 1, at positions 1 and 6 within Region 2, and at positions 1 and 3 within Region 3 (including the nucleotides in either the sense strand or the anti-sense strand at these positions).

Detection of Regions 1-6 of HLA-B*5801 can be achieved respectively by identifying nucleotides at positions 1, 2, and 5 within Region 1, at positions 1, 4, 6, 7, 8, 15, 16, and 20 within Region 2, at positions 2, 4, 5, 8, and 9 within Region 3, at positions 3 and 5 within Region 4, at positions 1 and 9 within Region 5, and at positions 3 and 10 within Region 6.

The present invention also provides a kit for detecting a genetic allele, e.g., HLA-B*1502 or HLA-B*5801. In one example, this kit contains a first probe and a second probe, each targeting a region selected from Regions 1-6 of HLA-B*1502 or Regions 1-6 of HLA-B*5801. The two probes target different regions. The kit can further include a third probe that targets an internal control allele. It can also include one or more additional probes for detecting one or more additional regions within HLA-B*1502 or HLA-B*5801.

Further provided is a method for determining whether a compound is a candidate that induces an ADR (e.g., SJS/TEN, HSS, or a milder cutaneous ADR) in a patient carrying an HLA allele (e.g., HLA-B*1502, HLA-B*5801, or HLA-B*4601) associated with the ADR induced by a drug (e.g., CBZ, allopurinol, or phenytoin). This method includes the steps of: (1) isolating T cells from an ADR patient carrying an HLA allele associated with the ADR, (2) expanding T cells reactive to the drug that induces the ADR, (3) isolating antigen-presenting cells from the patient, (4) contacting the expanded T cells with a compound in the presence of the APCs, and (5) examining whether the compound activates the expanded T cells. A compound that activates the T cells is a candidate that induces the ADR in a patient carrying the same HLA allele.

A patient has a "risk" for an ADR if the probability of the patient to develop an ADR is higher than the probability of the general population to develop the ADR. The probability of the patient to develop the ADR is at least about 1.5 fold, more preferably at least about 2 fold, still more preferably at least about 3, 4, 5, 6, 7, 8 or 9 fold, and most preferably at least about 10 fold as high as the probability of the general population to develop the ADR. The probability can be determined by any method known in the art, such as by using the incidence of risk factors. For example, a given risk factor is present in 5% of the general population. If this factor is present in 10% of the patients who have an ADR, then the probability of a patient with this risk factor to develop the ADR is 2 fold as high as the probability of the general population to develop the ADR.

A "risk factor" for an ADR is a factor that is associated with the ADR. The sensitivity of a risk factor is preferably at least about 40%, more preferably at least about 50%, 60%, 70%, 80%, 85% or 90%. Most preferably, the sensitivity is at least 95%. The "sensitivity" of a risk factor for predicting an ADR is the percentage of patients with the ADR that possess the risk factor. In other words, if every SJS patient has allele A, the sensitivity of allele A for predicting SJS is 100%. If 20 out of 40 SJS patients have allele B, then the sensitivity of allele B for predicting SJS is 50%.

An "equivalent genetic marker" of an allele of interest refers to a genetic marker that is linked to the allele of interest, i.e., it displays a linkage disequilibrium with the allele of interest.

"Pharmacogenomics profiling" refers to the determination of genetic factors present in a subject that are associated with diseases or medical conditions, particularly adverse reactions to drugs. Typically, a panel of genetic factors is determined in pharmacogenomics profiling, and the factors may or may not be associated with the same disease, medical condition, or reaction to drug.

A drug compound, as used herein, refers to a compound that is a drug or the same as the drug except that at least one hydrogen in the drug is substituted with a halo, hydroxyl, acylamino, alkyl, alkenyl, alkynyl, alkoxy, aryloxy, aryl, aryloxyaryl, carboxyl, carboxylalkyl, carboxyl-substituted alkyl, carboxyl-cycloalkyl, carboxylsubstituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted alkyl, substituted alkoxy, substituted aryl, substituted aryloxy, substituted aryloxyaryl, substituted cycloalkyl, heteroaryl, substituted heteroaryl, heterocyclic or substituted heterocyclic group. The chemical groups are defined below. The subsistent can contain zero to ten, zero to six, zero to four, or zero to two carbon atoms.

As used herein, "alkyl" refers to alkyl groups having 1 to 10 carbon atoms or 1 to 6 carbon atoms. "Substituted alkyl" refers to an alkyl group, preferably of from 1 to 10 carbon atoms, having from 1 to 5 substituents selected from the group consisting of alkoxy, substituted alkoxy, acyl, acylamino, thiocarbonylamino, acyloxy, amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxylaryl, substituted aryloxyaryl, cyano, halogen, hydroxyl, nitro, carboxyl, carboxyalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxylsubstituted heterocyclic, cycloalkyl, substituted cycloalkyl, guanidino, guanidinosulfone thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted aryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic, mono- and di-alkylamino, mono- and di-(substituted alkyl)amino, mono and di-arylamino, mono- and di-(substituted aryl)amino, mono- and diheteroarylamino, mono- and di-(substituted heteroaryl) amino, mono- and diheterocyclic amino, mono- and di-(substituted heterocyclic) amino, unsymmetric disubstituted amines having different substituents selected from the group consisting of alkyl, substituted alkyl, aryl, substituted aryl, heteroaryl, substituted heteroaryl, heterocyclic and substituted heterocyclic; substituted alkyl groups having amino groups blocked by conventional blocking groups and alkyl/substituted alkyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic or —SO$_2$—NRR, where R is hydrogen or alkyl.

"Alkoxy" refers to the group "alkyl-O—," which includes, by way of example, methoxy, ethoxy, n-propoxy, iso-propoxy, n-butoxy, tert-butoxy, sec-butoxy, npentoxy, n-hexoxy, 1,2-dimethylbutoxy, and the like. "Substituted alkoxy" refers to the group "substituted alkyl-O—."

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O), cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Acylamino" refers to the group —C(O)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic; and where each R can be joined to form, together with the nitrogen atom, a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic—C(O)O—, and substituted heterocyclic—C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Alkenyl" refers to alkenyl group preferably having from 2 to 10 carbon atoms and more preferably 2 to 6 carbon atoms and having at least 1 and preferably from 1-2 sites of alkenyl unsaturation. "Substituted alkenyl" refers to alkenyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxylcycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic; mono- and di-alkylamino, mono- and di-(substituted alkyl)amino, mono and di-arylamino, mono- and di-(substituted aryl)amino, mono- and diheteroarylamino, mono- and di-(substituted heteroaryl)amino, mono- and diheterocyclic amino, mono- and di-(substituted heterocyclic) amino, unsymmetric di-substituted amines having different substituents selected from the group consisting of alkyl, substituted alkyl, aryl, substituted aryl, heteroaryl, substituted heteroaryl, heterocyclic and substituted heterocyclic and substituted alkenyl groups having amino groups blocked by conventional blocking groups (such as Boc, Cbz, formyl, and the like) and alkenyl/substituted alkenyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic or —SO$_2$ NRR, where R is hydrogen or alkyl.

"Alkynyl" refers to alkynyl group preferably having from 2 to 10 carbon atoms and more preferably 3 to 6 carbon atoms and having at least 1 and preferably from 1-2 sites of alkynyl unsaturation. "Substituted alkynyl" refers to alkynyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, arninocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxylcycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)2-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic, mono- and di-alkylamino, mono- and di-(substituted alkyl)amino, mono and di-arylamino, mono- and di-(substituted aryl)amino, mono- and diheteroarylamino, mono- and di-(substituted heteroaryl)amino, mono- and di-heterocyclic amino, mono- and di-(substituted heterocyclic) amino, unsymmetric di-substituted amines having different substituents selected from the group consisting of alkyl, substituted alkyl, aryl, substituted aryl, heteroaryl, substituted heteroaryl, heterocyclic and substituted heterocyclic; substituted alkynyl groups having amino groups blocked by conventional blocking groups (such as Boc, Cbz, formyl, and the like), and alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic or —SO$_2$NRR, where R is hydrogen or alkyl.

"Aminoacyl" refers to the groups —NRC(O)alkyl, —NRC(O)substituted alkyl, —NRC(O)cycloalkyl, —NRC(O)substituted cycloalkyl, —NRC(O)alkenyl, —NRC(O)-substituted alkenyl, —NRC(O)-alkynyl, —NRC(O)-substituted alkynyl, —NRC(O)-aryl, —NRC(O)substituted aryl, —NRC(O)heteroaryl, —NRC(O)substituted heteroaryl, —NRC(O)heterocyclic, and —NRC(O)substituted heterocyclic, where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the groups —NRC(O)O-alkyl, —NRC(O)O-substituted alkyl, —NRC(O)O-alkenyl, —NRC(O)O-substituted alkenyl, —NRC(O)O alkynyl, —NRC(O)O-substituted alkynyl, —NRC(O)O-cycloalkyl, —NRC(O)O substituted cycloalkyl, —NRC(O)O-aryl, —NRC(O)O-substituted aryl, —NRC(O)Oheteroaryl, —NRC(O)O-substituted heteroaryl, —NRC(O)O-heterocyclic, and —NRC(O)O-substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxycarbonylamino" refers to the groups —OC(O)NRR, —OC(O)NR-alkyl, —OC(O)NR-substituted alkyl, —OC(O)NR-alkenyl, —OC(O)NR-substituent alkenyl, —OC(O)NR-alkynyl, —OC(O)NR-substituted alkynyl, —OC(O)NR-cycloalkyl, —OC(O)NR-substituted cycloalkyl, —OC(O)NR-aryl, —OC(O)NR-substituted aryl, —OC(O)NR-heteroaryl, —OC(O)NR-substituted heteroaryl, —OC(O)NR-heterocyclic, and —OC(O)NR-substituted heterocyclic where R is hydrogen or alkyl, and where each R can be joined to form, together with the nitrogen atom, a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryl" or "Ar" refers to an unsaturated aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like). Preferred aryls include phenyl and naphthyl.

Substituted aryl refers to aryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxylsubstituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —SO(O)$_2$-alkyl, —S(O)$_2$-substituted alkyl, —S(O)$_2$-cycloalkyl, —S(O)$_2$-substituted cycoalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—

NR-substituted aryl, —NRS(O)$_2$—NR-heteroaryl, —NRS(O)$_2$—NR-substituted heteroaryl, —NRS(O)$_2$—NR-substituted —NRS(O)$_2$—NR-substituted heterocyclic, mono- and di-alkylamino, mono- and di-(substituted alkyl)amino, mono- and di-arylamino, mono- and di-(substituted aryl)amino, mono and di-heteroarylamino, mono- and di-(substituted heteroaryl)amino, mono- and di-heterocyclic amino, mono- and di-(substituted heterocyclic) amino, unsymmetric di-substituted amines having different substituents selected from the group consisting of alkyl, substituted alkyl, aryl, substituted aryl, heteroaryl, substituted heteroaryl, heterocyclic, substituted heterocyclic, amino groups on the substituted aryl blocked by conventional blocking groups (such as Boc, Cbz, formyl, and the like), and —SO$_2$NRR, where R is hydrogen or alkyl.

"Substituted aryloxyaryl" refers to aryloxyaryl groups substituted with from 1 to 3 substituents on either or both aryl rings selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic, mono- and di-alkylamino, mono- and di-(substituted alkyl)amino, mono- and di-arylamino, mono- and di-(substituted aryl)amino, mono- and di-heteroarylamino, mono- and di-(substituted heteroaryl)amino, mono- and di-heterocyclic amino, mono- and di-(substituted heterocyclic) amino, unsymmetric di-substituted amines having different substituents selected from the group consisting of alkyl, substituted alkyl, aryl, substituted aryl, heteroaryl, substituted heteroaryl, heterocyclic, substituted heterocyclic, amino groups on the substituted aryl blocked by conventional blocking groups and substituted with —SO$_2$NRR, where R is hydrogen or alkyl.

"Cycloalkyl" refers to cyclic alkyl groups of from 3 to 8 carbon atoms having a single cyclic ring including, by way of example, cyclopropyl, cyclobutyl, cyclopentyl, cyclooctyl and the like. Excluded from this definition are multi-ring alkyl groups such as adamantanyl. "Cycloalkenyl" refers to cyclic alkenyl groups of from 3 to 8 carbon atoms having single or multiple unsaturation but which are not aromatic.

"Substituted-cycloalkyl" and "substituted cycloalkenyl" refer to a cycloalkyl and cycloalkenyl groups, preferably of from 3 to 8 carbon atoms, having from 1 to 5 substituents selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxylsubstituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic, mono- and di-alkylamino, mono- and di-(substituted alkyl) amino, mono and di-arylamino, mono- and di-(substituted aryl)amino, mono- and di-heteroarylamino, mono- and di-(substituted heteroaryl)amino, mono- and di-heterocyclic amino, mono- and di-(substituted heterocyclic) amino, unsymmetric di-substituted amines having different substituents selected from the group consisting of alkyl, substituted alkyl, aryl, substituted aryl, heteroaryl, substituted heteroaryl, heterocyclic and substituted heterocyclic, substituted alkynyl groups having amino groups blocked by conventional blocking groups (such as Boc, Cbz, formyl, and the like) and alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic or —SO$_2$NRR, where R is hydrogen or alkyl.

"Cycloalkoxy" refers to —O-cycloalkyl groups. "Substituted cycloalkoxy" refers to —O-substituted cycloalkyl groups.

"Halo" refers to fluoro, chloro, bromo and iodo and preferably is either chloro or bromo.

"Heteroaryl" refers to an aromatic carbocyclic group of from 2 to 10 carbon atoms and 1 to 4 heteroatoms selected from the groups consisting of oxygen, nitrogen and sulfur within the ring. Such heteroaryl groups can have a single ring (e.g., pyridyl or furyl) or multiple condensed rings (e.g., indolizinyl or benzothienyl). Preferred heteroaryls include pyridyl, pyrrolyl, indolyl and furyl.

"Substituted heteroaryl" refers to heteroaryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic, mono- and di-alkylamino, mono- and di-(substituted alkyl)amino, mono- and di-arylamino, mono- and di-(substituted aryl)amino, mono- and di-heteroarylamino, mono- and di-(substituted heteroaryl) amino, mono- and di-heterocyclic amino, mono- and di-(substituted heterocyclic) amino, unsymmetric di-substituted amines having different substituents selected from the group consisting of alkyl, substituted alkyl, aryl, substituted aryl, heteroaryl, substituted heteroaryl, heterocyclic and substituted heterocyclic, amino groups on the substituted aryl blocked by conventional blocking groups (such as Boc, Cbz, formyl, and the like), and —SO$_2$ NRR, where R is hydrogen or alkyl.

"Heteroaryloxy" refers to the group —O-heteroaryl and "substituted heteroaryloxy" refers to the group —O-substituted heteroaryl.

"Heterocycle" or "heterocyclic" refers to a saturated or unsaturated group having a single ring or multiple condensed rings, containing from 1 to 10 carbon atoms and from 1 to 4 heteroatoms selected from the group consisting of nitrogen, sulfur or oxygen within the ring. In fused ring systems, one or more of the rings can be aryl or heteroaryl.

"Substituted heterocyclic" refers to heterocycle groups which are substituted with from 1 to 3 substituents selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloakyl, carboxylaryl, carboxyl-substituted aryl, carboxylheteroaryl, carboxyl-substituted heteroaryl, carboxylheterocyclic, carboxylsubstituted heterocyclic, cycloalkyl, substituted cycloalkyl, guanidino, guanidinosulfone, thiol, thioalkyl, substituted thioalkyl, thioaryl, substituted thioaryl, thiocloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-alkyl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic, mono- and di-alkylamino, mono- and di-(substituted alkyl) amino, mono-and di-arylamino, mono- and di-(substituted aryl)amino, mono- and di-heteroarylamino, mono- and di-(substituted heteroaryl)amino, mono- and di-heterocyclic mono- and di-(substituted heterocyclic) amino, unsymmetric di-substituted amines having different substituents selected from the group consisting of alkyl, substituted alkyl, aryl, substituted aryl, heteroaryl, substituted heteroaryl, heterocyclic and substituted heterocyclic, substituted alkynyl groups having amino groups blocked by conventional blocking groups and alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic or —SO$_2$NRR, where R is hydrogen or alkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholino, thiomorpholino, piperidinyl, pyrrolidine, tetrahydrofuranyl, and the like.

"Heterocyclyloxy" refers to the group —O-heterocyclic, and "substituted heterocyclyloxy" refers to the group —O-substituted heterocyclic.

The details of one or more implementations of the invention are set forth in the description below. Other features, objects, and advantages of the invention will be apparent from the description and drawings, and from the claims.

DESCRIPTION OF DRAWINGS

FIG. 1 shows the nucleotide sequence of HLA-B*1502, including Regions 1-6.

FIG. 2 shows the nucleotide sequence of HLA-B*5801, including Regions 1-6.

DETAILED DESCRIPTION OF THE INVENTION

Figure 3:
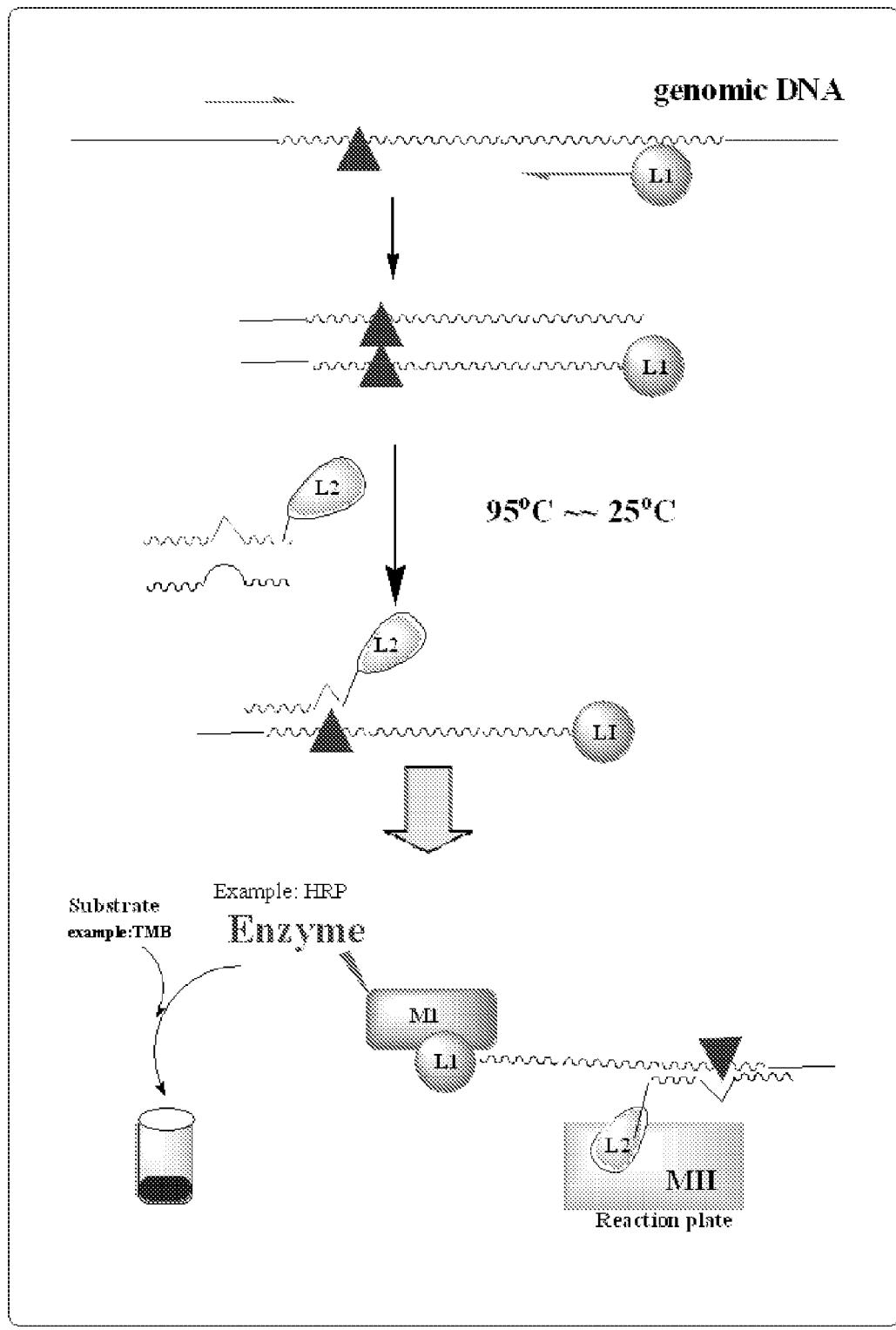
FIG. 3 is a schematic diagram illustrating Competitive Sequence Specific Oligonucleotide-ELISA assay (CSSO-ELISA).

Some evidence suggests that the pathogenesis of several similar multisystem ADRs involves MHC-restricted presentation of a drug or its metabolites, which either directly bind to MHC molecules or bind to endogenous proteins, and activation of T cells (Svensson et al., Pharmacol. Rev., 53(3):357-379, 2000). Skin-infiltrating CD830 cytotoxic T cells were found to be dominant in the bullous reactions such as SJS/TEN (Hari et al., Clin. Exp. Allergy, 31(9):1398-1408, 2001), whereas CD4+ helper T cells were characteristic of milder cutaneous ADRs, such as maculopapular rash (Pichler et al., Int. Arch. Allergy Immunol., 113(1-3):177-180, 1997).

It was discovered that HLA-B*1502, HLA-B*5801, and HLA-B*4601 are respectively associated with SJS/TEN induced by CBZ, with SJS/TEN/HSS induced by allopurinol, and with milder cutaneous ADRs (e.g., maculopapular rash, erythema multiforme, urticaria, or fixed drug eruption) induced by CBZ. Thus, these HLA-B alleles are useful genetic markers for determining whether a patient is at risk for developing ADRs (e.g., SJS, TEN, HSS, or milder cutaneous ADRs) induced by CBZ compounds, allopurinol compounds, or drugs otherwise having similar structures thereof.

CBZ, also known as Tegretol, Tegol, G-32883, Biston, Calepsin, Carbatrol, Epitol, Finlepsin, Sirtal, Stazepine, Telesmin, or Timonil, is an aromatic anticonvulsant. Other aromatic anticonvulsants, including phenytoin (Dilantin) and phenobarbital, cause similar ADRs as CBZ. Therefore, HLA-B*1502 can be employed to assess the risk for ADRs to these other aromatic anticonvulsants as well. The aromatic anticonvulsants for which HLA-B*1502 can be used as a risk factor also include compounds or metabolites of CBZ, phenytoin or phenobarbital. Metabolites of these drugs are known in the art (see, e.g., Gennis et al., 1991; Leeder, Epilepsia, 39 Suppl. 7:S8-16, 1998; Naisbitt et al., Mol. Pharmacol., 63(3):732-741, 2003), such as CBZ-10,11 epoxide, CBZ-10,11-diol, CBZ-2,3-diol, dihydro CBZ, CBZ catechol and CBZ o-quinone, p-hydroxy phenytoin, phenytoin dihydrodiol, phenytoin catechol, phenytoin methylcatechol, and phenytoin o-quinone.

Allopurinol is a drug for hyperuricemia and chronic gout.

The present invention provides a method of predicting whether a patient is at risk for developing ADRs, particularly SJS, TEN, or HSS, based on the presence of certain HLA alleles or their equivalent genetic markers in that patient.

In one example, the presence of HLA-B*1502 in a patient indicates that the patient is at risk for developing SJS/TEN induced by CBZ compounds, compounds otherwise structurally similar to CBZ, or metabolites thereof. Table I shows examples of compounds that can induce SJS/TEN in an HLA-B*1502 carrier.

TABLE I

Drug compounds associated with SJS in patients with HLA-B* 1502

| Names of active ingredients or the Brand Name | Structures of the active ingredient |
|---|---|
| carbamazepine, Epitol, Tegretol, Microtrol Bipotrol, carbamazepine, carbamazepine, Pharmavene, carbamazepine, Carbatrol, SPD-417 5H-Dibenz[b,f]azepine-5-carboxamide [CAS] | |
| Oxcarbazepine, Trileptal GP-47680, GP-47779, GP-47779 MHD, KIN-493, oxacarbazepine, TRI-476, TRI-477, TRI-477 (MHD), Trileptal NP, [CAS]: 5H-Dibenz[b,f]azepine-5-carboxamide, 10,11-dihydro-10-oxo | |
| licarbazepine BIA-2-093 BIA-2-005 [CAS]: (S)-(-)-10-acetoxy-10,11-dihydro-5H-dibenzo/b,f/azepine-5-carboxamide | |
| modafinil, Sparlon(New Formulation drug), [CAS]: Acetamide, 2-[(diphenylmethyl)sulfinyl]- | |

In another example, the presence of HLA-B*5801 in a patient indicates that the patient is at risk for SJS/TEN or HSS induced by allopurinol compounds, compounds otherwise structurally similar to allopurinol, or metabolites thereof. Table II shows examples of compounds that can induce SJS/TEN or HSS in patients carrying HLA-B*5801.

TABLE II

Drug compounds associated with SJS in patients carrying HLA-B* 5801

| Names | Structure of the active ingredient |
|---|---|
| Allopurinol, Aloprim, Zyloprim, Apo-Allopurinol, Purinol | |

TABLE II-continued

Drug compounds associated with SJS in patients carrying HLA-B* 5801

| Names | Structure of the active ingredient |
|---|---|
| Oxypurinol, Oxyprim [CAS]: 1H-Pyrazolo[3,4-d]pyrimidine-4,6(5H,7H)-dione | |
| Febuxostat, TEI-6720, TMX-67 [CAS]: 5-Thiazolecarboxylic acid, 2-[3-cyano-4-(2-methylpropoxy)phenyl]-4-methyl- | |
| Y-700 1-(3-Cyano-4-neopentyloxyphenyl)pyrazole-4-carboxylic acid | |
| modafinil, Sparlon(New Formulation drug), [CAS]: Acetamide, 2-[(diphenylmethyl)sulfinyl]- | |

In yet another example, the presence of HLA-B*4601 in a patient indicates that the patient is at risk for developing mild cutaneous ADRs, e.g., maculopapular rash, induced by CBZ.

Other HLA-B alleles can also be predispositive for cutaneous ADRs. For example, ankylosing spondylitis is strongly associated with HLA-B27 alleles, such as B*2701-B*2723. (Khan, Curr. Opin. Rheumatol., 12(4):235-238, 2000; Feltkamp et al., Curr. Opin. Rheumatol., 13(4):285-290, 2001).

The presence of a genetic marker (e.g., an HLA allele) can be determined by direct detection of that marker or particular regions within it. Genomic DNAs for allele detection can be prepared from a patient by methods well known in the art, e.g., PUREGENE DNA purification system from Gentra Systems, Minnesota. Detection of a region within a genetic marker of interest includes examining the nucleotide(s) located at either the sense or the anti-sense strand within that region. Methods known in the art can be used to detect a particular region, e.g., Sequence specific oligonucleotides-hybridization, Real-time PCR, or CSSO-ELISA (M. Hiratsuka et al, J. of Biochemical and Biophysic. Methods, 67:87-94, 2006).

The presence of HLA-B*1502 can be determined by detecting at least two of Regions 1-6 shown in FIG. 1 (SEQ ID NOS 1 and 2 disclosed respectively in order of appearance). The presence of these regions can be determined by detecting nucleotides at certain positions within these regions, e.g., positions 1 and 3 in Region 1, positions 1 and 6 in Region 2, and positions 1 and 3 in Region 3. Presence of any two of Regions 1-6 indicates that the patient is an HLA-B*1502 carrier.

The presence of HLA-B*5801 can be determined by detecting at least two of Regions 1-6 shown in FIG. 2 (SEQ ID NOS 3 & 4 disclosed respectively in order of appearance). The presence of these regions can be determined by detecting the nucleotides at certain positions within these regions, e.g., positions 1, 2, and 5 in Region 1, positions 1, 4, 6, 7, 8, 15, 16, and 20 in Region 2, positions 2, 4, 5, 8, and 9 in Region 3, positions 3 and 5 in Region 4, positions 1 and 9 in Region 5, and positions 3 and 10 in Region 6. Presence of any two of Regions 1-6 indicates that the patient is an HLA-B*5801 carrier.

The DNA products obtained from PCR can be detected using sequence-specific probes, e.g., hydrolysis probes from TaqMan, Beacons, Scorpions; or hybridization probes These probes are designed such that they bind to the regions of interest, e.g., Regions 1-6 of HLA-B*1502 or Regions 1-6 of HLA-B*5801. The PCR products also can be detected by DNA-binding agents, e.g., SYBR® Green.

The presence of an allele of interest also can be determined by detecting genetic markers equivalent to the allele. Genetic markers near the allele of interest tend to co-segregate, or show a linkage disequilibrium, with the allele. Consequently, the presence of these markers (equivalent genetic markers) is indicative of the presence of the allele of interest, which, in turn, is indicative of a risk for ADR development. Exemplary genetic markers equivalent to HLA-B*1502 include DRB1*1202, Cw*0801, Cw*0806, A*1101, and MICA*019. Exemplary markers equivalent to HLA-B*5801 include A*3303, Cw*0302, DRB1*0301, and MICA*00201.

An equivalent genetic marker can be of any type, e.g., an HLA allele, a microsatellite marker, or a single nucleotide polymorphism (SNP) marker. A useful equivalent genetic marker is normally about 200 kb or less (e.g., 100 kb, 80 kb, 60 kb, 40 kb, or 20 kb) from the allele of interest. Methods described above or known in the art can be used to detect the presence or absence of an equivalent genetic marker.

Alternatively or in addition, RNAs, cDNAs, or protein products of alleles of interest can be detected to determine the presence or absence of the allele. For example, serotyping or microcytotoxity methods can be used to determine the protein product of an HLA allele.

To further increase the accuracy of risk prediction, the allele of interest and/or its equivalent genetic marker can be determined along with the genetic markers of accessory molecules and co-stimulatory molecules which are involved in the interaction between antigen-presenting cells and T-cells. These genetic markers include microsatellite and single nucleotide polymorphism (SNP) markers. The accessory and co-stimulatory molecules include cell surface molecules (e.g., CD80, CD86, CD28, CD4, CD8, T cell receptor (TCR), ICAM-1, CD11a, CD58, CD2, etc.) and inflammatory or pro-inflammatory cytokines, chemokines (e.g., TNF-α), and mediators (e.g., complements, apoptosis proteins, enzymes, extracellular matrix components, etc.). Also of interest are genetic markers of drug metabolizing enzymes which are involved in the bioactivation or detoxification of drugs. These genetic markers also include microsatellite and SNP markers. The drug metabolizing enzymes include phase I enzymes (e.g., cytochrome P450 superfamily etc.) and phase II enzymes (e.g., microsomal epoxide hydrolase, arylamine N-acetyltransferase, UDP-glucuronosyl-transferase, etc.).

The present invention further provides a method for pharmacogenomic profiling. A panel of genetic factors is determined for a given individual, and each genetic factor is associated with the predisposition for a disease or medical condition, including ADRs. In the present method, the panel of genetic factors includes at least one allele selected from the group consisting of HLA-B*1502, HLA-B*5801 and HLA-B*4601. The panel can include two alleles or all three alleles from the group. In addition to HLA-B*1502, 5801 and/or 4601, the panel can include any other known genetic factors, such as thiopurine methyltransferase and genes for the long-QT syndrome. The genetic markers for accessory molecules, co-stimulatory molecules and/or drug metabolizing enzymes described above can also be included.

Also within the scope of the invention is a kit containing probes for detecting genetic markers, e.g., HLA-B*1502, HLA-B*5801 or HLA-B*4601. The term "probe" used herein refers to any substance useful for detecting another substance. Thus, a probe can be an oligonucleotide or conjugated oligonucleotide that specifically hybridizes to a particular region within an allele of interest. The conjugated oligonucleotide refers to an oligonucleotide covalently bound to chromophore or a molecules containing a ligand (e.g., an antigen), which is highly specific to a receptor molecular (e.g., an antibody specific to the antigen). The probe can also be a PCR primer, together with another primer, for amplifying a particular region within the allele of interest. Further, the probe can be an antibody that recognizes an allele of interest or a protein product of the allele. Optionally, the kit can contain a probe that targets an internal control allele, which can be any allele presented in the general population, e.g. GAPDH, β-actin, KIR. Detection of an internal control allele is designed to assure the performance of the kit.

The kit can further include tools and/or reagents for collecting biological samples from patients, as well as those for preparing genomic DNA, cDNAs, RNAs or proteins from the samples. For example, PCR primers for amplifying the relevant regions of the genomic DNA may be included. The kit can also contain probes for genetic factors useful in pharmacogenomic profiling, e.g., thiopurine methyltransferase.

In one example, the kit contains a first probe and a second probe, each for detecting a region selected from Regions 1-6 of HLA-B*1502 or from Regions 1-6 of HLA-B*5801. The first and second probes target different regions. These two probes can be a pair of PCR primers, or labeled oligonucleotides useful in hybridization assays. Optionally, the kit can include a third probe for detecting an internal control allele. It can also include additional probes for detecting additional regions within HLA-B*1502 or HLA-B*5801.

In yet another aspect, this invention provides a method of identifying a drug compound that induces an ADR (e.g., SJS/TEN or HSS) in a patient carrying an HLA allele associated with the ADR (e.g., HLA-B*1502, HLA-B*5801 or HLA-B*4601). It is suggested that drugs can be presented by certain HLA complexes to activate T lymphocytes, consequently inducing ADRs. T cells reactive to these drugs are suggested to be involved in the development of ADRs induced by these drugs. Thus, compounds that can activate these T cells are candidates for inducing ADRs in a patient carrying one or more HLA alleles associated with these ADRs. As a result, this method can be used as a screening method in new drug development to find out drug compounds that could induce such ADRs.

Genotyping can be performed on an ADR patient to determine whether the patient carries an HLA allele associated with the disease. T lymphocytes and antigen-presenting cells (e.g., B cells or monocytes) can be isolated from the patient and cultured in vitro following methods well known in the art. (Naisbitt D J, Mol Pharmacol. 2003 March; 63(3):732-41, Wu et al, J Allergy Clin Immunol. 2006 July; 118(1):233-41. E-published on 2006 Apr. 27). B cells so isolated can be transformed by Epstein-Bar virus to generate B cell lines. T cells reactive to a drug can be expanded in the presence of both the drug and autologous antigen-presenting cells. The expanded T cells can then be exposed to a test compound in the presence of autologous antigen-presenting cells to determine whether the test compound can activate the T cells. If so, the test compound is a candidate that can induce the ADR in a patient carrying the same HLA allele.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

EXAMPLE 1

Detection of HLA-B*1502 and HLA-B*5801 Using Real-Time PCR

Genomic DNAs were extracted from a patient's blood or saliva. Three pairs of PCR primers each targeting Regions 1 and 5, Regions 1 and 4, or Regions 1, 3 and 4 of HLA-B*1502 (see FIG. 1) were synthesized. In addition, one pair of primers targeting Regions 2 and 4 of HLA-B*5801 (see FIG. 2) were synthesized. The targeted regions were amplified and detected using SYBR® Green Real-Time PCR system (Applied Biosystem). Briefly, the primers, the genomic DNAs, and the Power SYBR® Green PCR master mixture (included in the real-time PCR system) were mixed together and the PCR was carried out by: (i) activating polymerase at 95° C. for 10 minutes, (ii) denaturing at 95° C. for 15 seconds and annealing/elongating DNA chains at 71° C. for 1 minute, (iii) conducting 40 cycles of denaturing/annealing/elongating, and (iv) disassociating the amplified product from its template at 95° C. for 15 seconds, and 60° C. for 1 minute. PCR amplification of a killer-cell immunoglobulin-like receptor (KIR) was applied as an internal control. The presence or absence of HLA-B*1502 or HLA-B*5801 in a patient was determined based on the Ct value of HLA-B*1502 or HLA-B*5801 and the difference of Ct values (ΔCt value) between HLA-B*1502/HLA-B*5801 and KIR. The Ct value (threshold cycle) is determined by identifying the cycle number at which the reporter dye emission intensity is above background noise. The threshold cycle is determined at the most exponential phase of the reaction and is more reliable than end-point measurements of accumulated PCR products used by traditional PCR methods. The threshold cycle is inversely proportional to the copy number of the target template, the greater the template number, the lower the threshold cycle measured.

170 genomic DNA samples extracted from human B cell lines and 35 genomic DNA samples prepared from human blood or saliva were tested for detecting the presence of HLA-B*1502 following the method described above. The Ct values of HLA-B*1502 and KIR were in the range of 23-27 and 19-25, respectively. The HLA-B*1502 were recognized as positive when the range of ΔCt between HLA-B*1502 and KIR was smaller than 7. In these 170 supercontrol, 15 gDNA with HLA-B*1502 were present and were verified by Dynal SSO kits, and the results indicate that both the sensitivity and specificity of this method reach >99%.

170 genomic DNA samples extracted from human B cell lines and 87 genomic DNA samples prepared from human blood or saliva were tested for detecting the presence of HLA-B*5801 following the method described above. For DNA samples derived from HLA-B*5801 positive patients, the Ct values of HLA-B*5801 and KIR were in the range of 22-28 and 10-26, respectively. The HLA-B*5801 were recognized as positive when the range of ΔCt between HLA-B*5801 and KIR was smaller than 7. For DNA samples derived from HLA-B*5801 negative patients, the Ct value of HLA-B*5801 was about 34 and the ΔCt was greater than 13. In all the samples, 51 gDNA were found HLA-B*5801 positive and were verified by Dynal SSO kits. These results indicate that both the sensitivity and specificity reached >99%.

EXAMPLE 2

Detection of HLA-B*1502 and HLA-B*5801 Using CSSO-ELISA

The procedures for carrying out CSSO-ELISA are outlined in FIG. 3.

In general, using genomic DNAs as templates, PCRs were conducted to produce products which contain the specific regions shown in FIG. 1 or FIG. 2. Either the Forward primer or the Reversed Primer was labeled with a Ligand I (LI), which was recognizable by the Molecular I linked with an enzyme (e.g. HRP) The PCR reactions were designed and conducted to produce the products containing one or more specific regions, i.e., Regions 1-6 of HLA-B*1502 or Regions 1-6 of HLA-B*5801. Two competitive sequence specific oligonucleotides (CSSO1 and CSSO2) were designed. CSSO1 specifically recognizes one of Regions 1-6 of HLA-B*1502 or Regions 1-6 of HLA-B*5801, and CSSO2 was designed to prime to the common type of HLA-B*15 (i.e. non-B*1502 alleles or non-B*-5801. The CSSO1 was labeled with Ligand 2, which is recognizable by Molecular II coated onto a reaction plateor strip. The PCR products thus obtained were hybridized with the two CSSOs on the reaction plate or a strip. After washing away any free molecule, substrate of the enzyme was added to the reaction plate. The enzymatic reaction, signaled by the presence of a color, is indicative of the presence of HLA-B*1502 or HLA-B*5801.

EXAMPLE 3

Correlation between CBZ-Induced SJS/TEN and HLA-B*1502

A total of 238 ADR patients (Mongoloids or Mongoloid descendents) were recruited either from Chang Gung Memorial Hospital or from several other medical centers throughout Taiwan for this study. Their drug-taking history including dosage and duration, and the phenotypes of ADRs were recorded. The diagnostic criteria of clinical morphology were defined according to Roujeau, J. Invest Dermatol., 102(6): 28S-30S, 1994. For example, SJS was defined as skin detachment of less than 10% of body-surface area, overlap SJS-TEN as skin detachment of 10-30%, and TEN as greater than 30%. SJS, overlap SJS-TEN and TEN are collectively referred to as SJS/TEN.

For each patient, the suspected drug was withdrawn and the patient observed for symptoms. Patients who developed a cutaneous ADR that did not subside upon withdrawal of the drug were excluded.

According to the criteria described above, 112 patients were diagnosed with SJS/TEN and 126 patients had a milder hypersensitivity reaction to various drugs. Among the 112 SJS/TEN patients, 42 were exposed to CBZ (tegretol), 17 had taken allopurinol, and 53 were under medications other than CBZ and allopurinol.

73 tegretol-tolerant patients were included as controls. Volunteers from the general population of Taiwanese (n=94; age range: 20 to 80 years) were also recruited. The study was approved by the institutional review board, and informed consent was obtained.

All of these patients were subjected to genotyping. Briefly, reagents for performing a reverse line blot assay using sequence-specific oligonucleotide (SSO) were purchased from DYNAL Biotech Ltd. (Bromborough, UK). PCR products were generated using biotinylated primers for the second and the third exons of the HLA class I or class II loci, and then hybridized to a line blot of SSO of probes immobilized on a nylon membrane. The presence of biotinylated PCR product bound to a specific probe is detected using streptavidin-horseradish peroxidase (HRP) and a chromogenic, soluble substrate to produce a blue "line" at the position of the positive probe. The probe reactivity pattern was interpreted by the genotyping software Dynal RELI™ SSO (DYNAL Biotech Ltd.; Bromborough, UK). Potential ambiguities were further resolved by sequence-based typing and DNA sequencing performed according to the IHWG Technical Manual (International Histocompatibility Working Group), see Genomic Analysis of the Human MHC DNA Based Typing for HLA Alleles and Linked Polymorphisms. Marcel G. J. Tilanus, Editor in Chief, ISBN No. 0-945278-02-0.

To some patients, SNP genotyping was performed using high throughput MALDI-TOF mass spectrometry. Briefly, primers and probes were designed using the SpectroDESIGNER software (Sequenom, San Diego, Calif., USA). Multiplex polymerase chain reactions (PCR) were performed, the unincorporated dNTPs were dephosphorylated using the shrimp alkaline phosphatase (Hoffman-LaRoche, Basel, Switzerland), followed by primer extension. The purified primer extension reaction was spotted onto a 384-element silicon chip (SpectroCHIP, Sequenom), analyzed using a Bruker Biflex III MALDI-TOF SpectroREADER mass spectrometer (Sequenom) and spectra processed with SpectroTYPER (Sequenom).

Allele frequencies in the different groups were compared by the Chi-square method with Yates correction by constructing 2×2 tables. P values were corrected for comparisons of multiple HLA alleles (Pc) by multiplying the raw P values by the observed number of HLA alleles present within the loci. Odds ratios were calculated with Haldane's modification, which adds 0.5 to all cells to accommodate possible zero counts.

As shown in Table 1, a DNA variant allele in the HLA-B locus (HLA-B*1502) was associated in patients with drug-induced SJS/TEN, particularly in patients receiving CBZ (tegretol).

TABLE 1

HLA-B*1502 frequency in 42 Taiwanese patients having CBZ-induced SJS/TEN

| Allele | Patients N = 42 | Controls1[a] N = 142 | Controls2[b] N = 94 | Controls3[c] N = 73 | $X^2$ | Odds Ratio | $P_c$ |
|---|---|---|---|---|---|---|---|
| B*1502 | 42 (100%) | 9 (6.3)% | | | 137.28 | 1194.47 | $3.6 \times 10^{-30}$ |
| B*1502 | 42 (100%) | | 5 (5.3%) | | 110.919 | 1383.2 | $2.15 \times 10^{-24}$ |
| B*1502 | 42 (100%) | | | 3 (4.1%) | 98.936 | 1712 | $9.1 \times 10^{-22}$ |

[a] patients who had milder ADRs other than SJS
[b] general Taiwanese population
[c] patients who are CBZ-tolerant
$X^2$, Chi-square with Yates correction
$P_c$, calculated by multiplying the raw P values by the observed number of HLA-B alleles (35).

HLA-B*1502 was detected in 42 of 42 (100%) SJS/TEN patients who received CBZ. The allele was also found in 17 of 53 (32%) SJS/TEN patients who received other drugs (8 phenytoin, 2 allopurinol, 2 amoxicillin, 1 sulfasalazine, 1 ketoprofen, 1 Ibuprofen, and 2 unknown drugs). Particularly, 8 of 17 patients (47.05%) who developed SJS/TEN after taking phenytoin also carried the HLA-B*1502 allele. On the other hand, the allele was only found in 4.1% (3/73) of the CBZ-tolerant group, 0% (0/32) of the phenytoin-tolerant group, 6.3% (9/142) of the patients who had milder ADRs other than SJS, and 5.3% (5/94) of the general population. By using the tolerant group as a control, the odds ratio, sensitivity, specificity, positive predictive value, and negative predictive value for B*1502 associated CBZ-induced SJS/TEN, were 1712, 100%, 95.89%, 96.0%, and 100%, respectively. With such a high predictive value and sensitivity, typing of this HLA-B allele can be used in identifying high-risk patients for drug-induced SJS/TEN, particularly CBZ or phenytoin induced SJS/TEN.

The mild ADRs induced by CBZ was found to be associated with another allele, HLA-B*4601. 10 out of 16 (62.5%) of the patients with these milder reactions to CBZ had HLA-B*4601. In contrast, the allele was only found in 26% (19/73) of the CBZ-tolerant group. The odds ratio for B*4601 associated CBZ-induced milder cutaneous ADRs was 4.73. Consequently, HLA-B*4601 can be used in the risk assessment for mild cutaneous ADR induced by CBZ.

TABLE 2

Phenotype/genotype data of patients having CBZ-induced cutaneous ADRs

| ID | Suspected drug | Phenotype | HLA-B Genotype |
|---|---|---|---|
| 1 | Carbamazepine | SJS | B*1502/B*3802 |
| 2 | Carbamazepine | SJS | B*1502/B*3501 |
| 3 | Carbamazepine | SJS | B*1502/B*4006 |
| 4 | Carbamazepine | SJS | B*1502/B*3802 |
| 5 | Carbamazepine | SJS | B*1502/B*3802 |
| 6 | carbamazepine, phenytoin | SJS | B*1502/B*3802 |
| 7 | Carbamazepine | SJS | B*1502/B*4001 |
| 8 | Carbamazepine | SJS | B*1502/B*3901 |
| 9 | Carbamazepine | SJS | B*1502/B*5801 |
| 10 | Carbamazepine | SJS | B*1502/B*5801 |
| 11 | Carbamazepine | SJS | B*1502/B*1525 |
| 12 | Carbamazepine | SJS | B*1502/B*4002 |
| 13 | Carbamazepine | SJS | B*1502/B*4006 |
| 14 | Carbamazepine | SJS | B*1502/B*5801 |
| 15 | Carbamazepine | Overlap SJS/TEN | B*1301/B*1502 |
| 16 | Carbamazepine | Overlap SJS/TEN | B*1502/B*3501 |
| 17 | Carbamazepine | SJS | B*1502/B*3802 |
| 18 | Carbamazepine | SJS | B*1502/B*4601 |
| 19 | Carbamazepine | SJS | B*1301/B*1502 |
| 20 | Carbamazepine | SJS | B*1502/B*5801 |
| 21 | Carbamazepine | SJS | B*1502/B*4601 |
| 22 | Carbamazepine, NSAID | SJS | B*1502 |
| 23 | Carbamazepine | SJS | B*1502/B*3501 |
| 24 | Carbamazepine | SJS | B*1502/B*4601 |
| 25 | Carbamazepine | SJS | B*1502/B*4601 |
| 26 | Carbamazepine | SJS | B*1502/B*5801 |
| 27 | Carbamazepine | SJS | B*1501/B*1502 |
| 28 | Carbamazepine | SJS | B*1502/B*4001 |
| 29 | Carbamazepine | SJS | B*1502 |
| 30 | carbamazepine, meloxicam, sulidanc, phenytoin | SJS | B*1502/B*5801 |
| 31 | Carbamazepine | SJS | B*1502/4601 |
| 32 | Carbamazepine | SJS | B*1502/5801 |
| 33 | Carbamazepine | SJS | B*1502/4601 |
| 34 | Carbamazepine | SJS | B*1502/5502 |
| 35 | Carbamazepine | SJS | B*1502 |
| 36 | carbamazepine, phenytoin | SJS | B*1502/4002 |
| 37 | Carbamazepine | SJS | B*1502/4001 |
| 38 | Carbamazepine | SJS | B*1502 |
| 39 | carbamazepine, phenytoin | SJS | B*1502 |
| 40 | Carbamazepine | Overlap SJS/TEN | B*1502/4001 |
| 41 | Carbamazepine | Overlap SJS/TEN | B*1502/4601 |
| 42 | Carbamazepine | SJS | B*1502/3802 |
| 43 | Carbamazepine | maculopapular rash | B*5801/B*4601 |
| 44 | Carbamazepine | erythema multiform | B*4001/B*4601 |
| 45 | Carbamazepine | maculopapular rash | B*1301/B*4001 |
| 46 | Carbamazepine | And angioedema | B*4601/B*5401 |
| 47 | Carbamazepine | maculopapular rash | B*4001/B*4601 |
| 48 | Carbamazepine, NSAID | maculopapular rash | B*4001/B*4001 |
| 49 | Carbamazepine | maculopapular rash | B*1301/B*5502 |
| 50 | Carbamazepine | lip swelling, oral and genital ulcer | B*4601/B*5801 |
| 51 | Carbamazepine | Maculopapular | B*4601/B*5801 |
| 52 | Carbamazepine | And angioedema | B*4001 |
| 53 | Carbamazepine | maculopapular rash | B*4001/B*5101 |
| 54 | Carbamazepine | maculopapular rash | B*1301/4001 |
| 55 | Carbamazepine | maculopapular rash | B*4001/B*4601 |
| 56 | Carbamazepine | erythema multiform | B*4601/B*5401 |
| 57 | Carbamazepine | maculopapular rash | B*4601 |
| 58 | Carbamazepine | erythema multiform | B*4601/5101 |

EXAMPLE 4

Correlation between Allopurinol-Induced SJS/TEN and HLA-B*5801

HLA-B*5801 was found to be associated with allopurinol-induced SJS/TEN. This HLA-B allele was found in all 17

(100%) SJS/severe ADR patients treated allopurinol (Tables 3 and 4), but was found in only 18% of the general Taiwanese population (odds ratio 155, sensitivity 100%, specificity 82%, positive predictive value 84.7%, negative predictive value 100%, Pc=3.7×10$^{-9}$). These results suggest that HLA-B*5801 is a useful genetic marker, either alone or in combination with other genetic markers, for assessing whether a patient taking allopurinol is at risk for developing SJS/TEN.

patients had a second attack within 2 days of re-exposure to allopurinol. Twelve patients received other drug(s) in addition to allopurinol, but their medical records revealed no ADRs when these concomitant medications were taken without allopurinol. All patients had hyperuricemia and/or gouty arthritis, as well as other chronic illnesses, including hypertension (14/31), chronic renal disease (16/31), and diabetes (9/31).

TABLE 3

HLA-B*5801 frequency in 17 Taiwanese patients with allopurinol-induced severe cutaneous ADRs

| Allele | Patients n = 17 | Controls1$^a$ n = 142 | Controls2$^b$ n = 94 | X$^2$ | odds ratio | P$_c$ |
|---|---|---|---|---|---|---|
| B*5801 | 17 (100%) | 26(18.3%) | | 47.2 | 153.86 | 2.1 × 10$^{-10}$ |
| B*5801 | 17 (100%) | | 17 (18.0%) | 41.7 | 155 | 3.7 × 10$^{-9}$ |

$^a$patients who had ADRs other than allopurinol-induced cutaneous ADR
$^b$general Taiwanese population
X$^2$, Chi-square with Yates correction
P$_c$, calculated by multiplying the raw P values by the observed number of HLA-B alleles (35).

TABLE 4

Phenotype/genotype data of patients with allopurinol-induced cutaneous ADRs

| Patient ID | Suspected drug | Phenotype | HLA-B Genotype |
|---|---|---|---|
| 59 | allopurinol | SJS | B*0705/B*5801 |
| 60 | allopurinol | SJS | B*4001/B*5801 |
| 61 | allopurinol | SJS | B*1554/B*5801 |
| 62 | allopurinol | SJS | B*3901/B*5801 |
| 63 | allopurinol | SJS | B*5801 |
| 64 | allopurinol | SJS | B*3901/B*5801 |
| 65 | allopurinol | SJS | B*3901/B*5801 |
| 66 | allopurinol | SJS | B*4001/B*5801 |
| 67 | Allopurinol | SJS | B*1502/B*5801 |
| 68 | allopurinol | SJS | B*4001/B*5801 |
| 69 | allopurinol | SJS and vasculitis on leg | B*4601/B*5801 |
| 70 | allopurinol | SJS, and lichenoid | B*4001/B*5801 |
| 71 | allopurinol | SJS | B*4002/B*5801 |
| 72 | allopurinol | SJS | B*4001/B*5801 |
| 73 | alloprinol | SJS | B*5101/B*5801 |
| 74 | allopurinol | TEN | B*1301/5801 |
| 75 | alloprinol | SJS | B*5801 |

EXAMPLE 5

Correlation between HLA-B*5801 and Allopurinol-Induced HSS

HLA-B*5801 was also found to be linked to allopurinol-induced HSS, which includes cutaneous rash (e.g., diffuse macuopapular, exfoliative dermatitis), fever, eosinophilia, atypical circulating lymphocytes, leukocytosis, acute hepatocellular injury, or worsening renal function (Arellano et al., Ann. Pharmacother., 27:337, 1993).

31 patients were studied, among which 21 had SJS, 3 SJS/TEN, 1 TEN, and 15 HSS. In all enrolled cases, allopurinol was regarded as the offending drug if the onset of ADR syndromes occurred within the first 2 months of allopurinol exposure and the ADRs symptoms disappeared upon withdrawal of the drug. Patients with any of the following conditions were excluded: absence of symptoms after re-exposure to allopurinol, and patients with milder skin eruption who did not meet the criteria of HSS, SJS or TEN.

The onset of HSS symptoms for all of the 31 patients was within the first 2 months of allopurinol exposure and 2

Ninety-eight gouty arthritis patients who had been on allopurinol for at least 6 months (mean=38 months, range=6-107 months) with no syndromes of ADRs were included as the allopurinol-tolerant control. The sex distribution of tolerant group is comparable to general prevalence of gout in Chinese people. Furthermore, 93 normal subjects served as the normal control group. The demographic variables of these 3 groups are shown in Table 5.

TABLE 5

Demographic variables, dosage and duration of allopurinol exposure in severe ADRs patients, tolerant patients, as well as normal subjects

| | Severe ADRs (n = 31) | Tolerant (n = 98) | Normal Subjects (n = 93) |
|---|---|---|---|
| Sex | | | |
| Male | 12 | 89 | 52 |
| Female | 19 | 9 | 41 |
| Age (years) | | | |
| Median (range) | 57.9 (18-91) | 57.3 (21-84) | 53.9 (22-91) |
| Allopurinol dosage (mg/day) | | | |
| Median (range) | 143.3 (50-300) | 159.2 (100-400) | None |
| Duration of allopurinol exposure | | | |
| Median (range) | 28.2 days (1-56) | 38 months (6-107) | None |

HLA-B*5801 allele was present in all 31 (100%) of the patients having allopurinol-induced severe ADRs, in 16 (16.3%) of the 98 allopurinol-tolerant patients (odds ratio 315, Pc<10$^{-15}$), and in 19 (20%) of the 93 normal subjects (odds ratio 241, Pc<10$^{-13}$). Relative to the allopurinol-tolerant group, the absence of HLA-B*5801 had a negative predictive value of 100% for allopurinol-induced ADRs, and the presence of this allele had a positive predictive value of 66%. Accordingly, HLA-B*5801 is a useful marker with high specificity (84%) and sensitivity (100%) for allopurinol-induced severe ADRs, including cutaneous ADRs (e.g., SJS/TEN or HSS) and allopurinol-induced DRESS (drug reaction with eosinophilia and systemic symptoms).

EXAMPLE 6

Genetic Markers Equivalent to HLA-B*1502 or HLA-B*5801

Genetic markers near an HLA allele of interest tend to co-segregate, or show a linkage disequilibrium, with the allele of interest. As a result, the presence of these markers (equivalent genetic markers) is indicative of the presence of the allele.

To test the incidence of potential equivalent genetic markers in patients with ADRs, several markers in the HLA-B*1502 haplotype were determined for their association with ADRs. Indeed, HLA markers of the HLA-B*1502 haplotype, such as DRB1*1202, Cw*0801, Cw*0806, A*1101, and MICA*019, had a significantly high frequency in SJS/TEN patients who had been exposed to CBZ (Table 6).

Markers associated with HLA-B*5801 were also determined. Allele distribution was analyzed in 4 patients who were homozygous for HLA-B*5801 and the ancestral haplotype of this allele was defined as including HLA-A*3303, Cw*0302, B*5801 and DRB1*0301. This ancestral haplotype was presented in 12 (38.7%) of the 31 allopurinol-ADRs patients (Table 7), but only in 7.1% of the tolerant patients and 9.7% of the normal subjects.

TABLE 6

Correlation between markers of B*1502- ancestral haplotypes and ADRs

|  | CBZ SJS/TEN (n = 42) | CBZ Milder (n = 16) | CBZ Tolerant (n = 73) | Allopurinol SJS/TEN (n = 17) | General Population (n = 94) |
|---|---|---|---|---|---|
| HLA-B*1502 | 42 (100%) | 0 (0%) | 3 (4.1%) | 1 (5.8%) | 5 (5.3%) |
| HLA-Cw*0801 | 38 (90%) | ND | 10 (13.7%) | 2 (11.7%) | 10 (10.6%) |
| HLA-Cw*0806 | 3 (7.1%) | ND | 0 (0%) | 0 (0%) | 0 (0%) |
| HLA-A*1101 | 31 (73.8%) | ND | ND | ND | 28 (29.8%) |
| HLA-DRB1*1202 | 35 (83.3%) | ND | ND | ND | 19 (20.2%) |

TABLE 7

Frequencies of individual or combined loci of HLA-B*5801 ancestral haplotype in patients with allopurinol-induced severe ADRs, allopurinol-tolerant patients, and in normal subjects

|  | Allopurinol-ADRs (n = 31) | Allopurinol-tolerant (n = 98) | Normal Subjects (n = 93) |
|---|---|---|---|
| B*5801 | 31 (100%) | 16 (16.3%)[1] | 19 (20.4%)[2] |
| Cw*0302 | 29 (93.5%) | 15 (15.3%) | 19 (20.4%) |
| A*3303 | 20 (64.5%) | 18 (18.4%) | 20 (21.5%) |
| DRB1*0301 | 21 (67.7%) | 14 (14.3%) | 14 (15.1%) |
| B*5801, Cw*0302 | 29 (93.5%) | 15 (15.3%) | 19 (20.4%) |
| B*5801, Cw*0302, A*3303 | 20 (64.5%) | 13 (13.3%) | 16 (17.2%) |
| B*5801, Cw*0302, DRB1*0301 | 19 (61.3%) | 9 (9.2%) | 10 (10.8%) |
| B*5801, Cw*0302, A*3303, DRB1*0301 | 12 (38.7%) | 7 (7.1%) | 9 (9.7%) |

[1]Odds ratio (Allopurinol-ADRs/Tolerant): 315 (95% CI, 18.3-5409.5), $p_c = 7.5 \times 10^{-16}$.
[2]Odds ratio (Allopurinol-ADRs/Normal): 241 (95% CI, 14.1-4111), $p_c = 6.1 \times 10^{-14}$.

MHC markers associated with HLA-B*5801 were also determined using short tandem repeat polymorphism assay (STRP). Briefly, twenty highly polymorphic microsatellite markers located in the MHC region were selected from NCBI database (i.e., D6S258, D6S2972, D6S510, D6S265, D6S388, D6S2814, HLAC_CA1, HLABC_CA2, MIB, MICA, TNFd, BAT2_CA, D6S273, D6S1615, DQCAR, G51152, D6S2414, D6S1867, D6S1560, and D6S1583). The average heterozygosity of these markers was 0.72 with an estimated spacing of 230 kb.

Primers were designed based on the sequences of these markers described in the database. PCRs were carried out to amplify and detect the presence or absence of these markers in patients using GeneAmp 9700 thermocyclers (Applied Biosystems, Foster City, Calif., USA) (in a 5-μl volume containing 10 ng of genomic DNA and 0.33 μM of each primer). Up to 6 PCR products having appropriate sizes and displaying fluorescent signals were pooled before capillary gel electrophoresis. The size of polymorphic amplicons was determined by electrophoresis of ABI 3730 DNA sequencer (Applied Biosystems), using the LIZ500 size standard as an internal size standard (Applied Biosystems). Allele sizing was calculated using the GENMAPPER program version 3.0 (Applied Biosystems). Allele calling and binning were performed using the SAS program. Three CEPH control individuals (1331-01, 1331-02, 1347-2) and H20 were included in all genotyping experiments for quality control purposes.

An allele block located between HLA-C and TNFd was found in the allopurinol-induced ADR patient group, but not in the allopurinol-tolerant group, using a linkage disequilibrium plot. In this block, a haplotype (MIB*358-MICA*206-TNFd*140) near the HLA-B allele was identified. The association of this haplotype with ADRs is consistent with the association of HLA-B*5801 with the same ADRs (p=0.0018). By using STRP markers and sequencing of the MICA allele, all allopurinol-induced ADR patients were found to carry the same B allele (B*5801), MICA allele (MICA*00201) and TNF STRP marker (TNFd*140). Except for one patient, all others were also found to carry the same MIB marker (MIB*358).

EXAMPLE 7

Cross-Reactivity of CBZ-Reactive T Cells to Oxcarbazepine and Licarbazepine

Two patients having CBZ-induced SJS/TEN were recruited from Chang Gung Memorial Hospital. One of the patients carried HLA-B*1502/B*4601, the other HLA-B*1502/B*5101. Genomic DNAs were extracted from the patients using PUREGENE DNA purification system (Gentra systems, Minnesota, USA). The HLA-B alleles were verified using sequence-specific oligonucleotide reverse line blots (DYNAL Biotech Ltd., Bromborough, U.K.).

Peripheral blood mononuclear cells (PBMCs) were isolated from the patients by Ficoll-Isopaque (Pharmacia Fine Chemicals, Piscataway, N.J.) density gradient centrifugation. A portion of the PBMCs were transformed by Epstein-Barr virus to establish autologous B-cell lines.

T cells reactive to CBZ were expanded as described below. PBMCs prepared from the patients were cultured in complete RPMI medium containing 10% heat-inactivated human serum, IL-2 (25 U/ml), and CBZ (25 µ/ml) (Sigma) in a 37° C., 5% $CO_2$ incubator for 7 days. The T cells were then expanded by co-culturing with irradiated (50 Gy) autologous B cells in the presence of CBZ for 10 days. After 2 cycles of the above co-culturing procedure, the CBZ-activated T cells were collected and subjected to ELISPOT assays (eBioscience).

The CBZ-reactive T cells were tested for their cross-reactivity to compounds e.g., CBZ 10, 11-epoxide, Oxcarbazepine (brand name: trileptal), Licarbazepine, and sunlindac. Briefly, T lymphocytes ($5 \times 10^3$ cells) were mixed with autologous B cells ($5 \times 10^4$ cells) in 200 µl RPMI medium containing 10% FBS in the presence or absence of a test compound. The cells were then incubated for 24 hours in the wells of an ELISPOT plate coated with anti-interferon γ antibodies (Millipore). After incubation, the supernatant of the cell culture was collected and interferon-γ contained therein was detected using antibody-mediated methods known in the art.

Results from this study indicate that CBZ-reactive T cells were cross-reactive to CBZ 10, 11-epoxide, Oxcarbazepine, and Licarbazepine, but not to Sulindac.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of assessing a risk of a human patient for developing an adverse drug reaction in response to a drug, comprising
   detecting the presence of HLA-B*1502 in a sample obtained from the patient, and
   correlating the presence of HLA-B*1502 in the sample with an increased risk for an adverse drug reaction in the patient in response to oxcarbazepine, wherein the adverse drug reaction is Stevens-Johnson syndrome or toxic epidermal necrolysis.

2. The method of claim 1, wherein the sample obtained from the patient is a DNA sample.

3. The method of claim 2, wherein the presence of the HLA allele is determined by hybridization with an oligonucleotide that specifically hybridizes to the allele.

4. The method of claim 2, wherein the DNA sample is obtained from peripheral blood, saliva, urine, or hair of the patient.

5. The method of claim 1, wherein the sample obtained from the patient is a RNA sample, a protein sample, a cell sample, or a serum sample.

6. The method of claim 5, wherein the sample is obtained from peripheral blood of the patient.

7. The method of claim 1, wherein the adverse drug reaction is Stevens-Johnson syndrome.

8. The method of claim 1, wherein the adverse drug reaction is toxic epidermal necrolysis.

* * * * *